(12) United States Patent
Feger

(10) Patent No.: US 6,672,759 B2
(45) Date of Patent: *Jan. 6, 2004

(54) METHOD FOR ACCOUNTING FOR CLAMP EXPANSION IN A COEFFICIENT OF THERMAL EXPANSION MEASUREMENT

(75) Inventor: Claudius Feger, Hopewell Junction, NY (US)

(73) Assignee: International Business Machines Corporation, Armonk, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 124 days.

(21) Appl. No.: 09/112,593

(22) Filed: Jul. 9, 1998

(65) Prior Publication Data

US 2002/0136262 A1 Sep. 26, 2002

Related U.S. Application Data

(60) Provisional application No. 60/058,648, filed on Jul. 11, 1997, and provisional application No. 60/059,891, filed on Sep. 24, 1997.

(51) Int. Cl.[7] ............................................... G01N 25/16
(52) U.S. Cl. .......................................... 374/56; 374/49
(58) Field of Search .............................. 374/55, 56, 49, 374/14, 46, 50, 51, 52, 53; 73/833

(56) References Cited

U.S. PATENT DOCUMENTS 2,656,712 A * 10/1953 Comstock .................... 374/56
3,234,778 A * 2/1966 Kreglo
3,583,208 A * 6/1971 Byrne, Jr. et al. ............ 374/56

(List continued on next page.)

FOREIGN PATENT DOCUMENTS

GB    2068123 A   *   8/1981   .................. 374/56
SU    1661634 A   *   7/1991   .................. 374/55
WO    98/29943     *   7/1998

OTHER PUBLICATIONS

Muller, R., et al., "Ultraprecision Dilatometer System for Thermal Expansion Measurements on Low Expansion Glasses," Thermal Conductivity 24 / Thermal Expansion 12, pp. 388–392 (Jan. 11, 1999).*

Wunderlich, B., Thermal Analysis, Academic Press, Boston, Mass., pp. 313–315, 321–325, 1990.*

(List continued on next page.)

*Primary Examiner*—Christopher W. Fulton
*Assistant Examiner*—Stanley J. Pruchnic, Jr.
(74) *Attorney, Agent, or Firm*—Thomas A. Beck; Daniel Morris

(57) ABSTRACT

The present invention is a method to eliminate the influence of clamp dimensional changes on the displacement measurement during the measurement of the coefficient of thermal expansion (CTE) of samples in tension. In a first embodiment clamp dimensional changes can be eliminated by making clamps from a material with near zero CTEs. In another embodiment clamp dimensional changes can be reduced by minimizing the CTE of the clamp material. Finally clamp dimensional changes are taken into account. This is achieved directly by subtracting a prerecorded baseline from the measurements; or by determining the CTE measurement for various sample lengths and obtaining the slope of a straight line through the points on a MD (measured displacement)/DT (temperature range of displacement measurement) versus sample length plot. The slope is the corrected CTE. Clamp dimensional changes can also be taken into account indirectly by obtaining a clamp displacement contribution (CDC) factor which allows to correct measured displacements to result the correct CTE.

39 Claims, 8 Drawing Sheets

U.S. PATENT DOCUMENTS

| | | | | |
|---|---|---|---|---|
| 3,680,357 A | * | 8/1972 | Clusener | 374/56 |
| 3,748,892 A | * | 7/1973 | McKendree Jr. et al. | 374/56 |
| 3,885,416 A | * | 5/1975 | Cooper | 374/56 |
| 4,019,365 A | * | 4/1977 | Woo | 374/55 |
| 4,054,049 A | * | 10/1977 | Egger | 374/56 |
| 4,313,679 A | * | 2/1982 | Wolff et al. | 374/55 |
| 4,393,718 A | * | 7/1983 | Gebhard et al. | 374/49 |
| 4,535,636 A | * | 8/1985 | Blackburn et al. | 374/55 |
| 4,923,307 A | * | 5/1990 | Gilmore et al. | 374/55 |
| 5,286,108 A | * | 2/1994 | Whatley et al. | 374/49 |
| 5,370,457 A | * | 12/1994 | Iizuka | 374/51 |
| 6,007,240 A | * | 12/1999 | Price | 374/55 |

OTHER PUBLICATIONS

Anter Corporation, "Principles of push–rod dilatometry," downloaded from "Anter.com" web site Jul. 14, 2001 (8 pages).*

Anter Corporation, "The use of thermomechanical analyzers (TMA) for dilatometric measurements," downloaded from "Anter.com" web site Jul. 14, 2001 ( 1 page).*

S. F. Jacobs, J. N. Bradford and J. W. Berthold III, "Ultra-precise Measurement of Thermal Coefficients of Expansion," App. Opt. 9(11): 2477–80 (Nov. 1970).*

Wolff, E. G., "Thermal Expansion of Thin Films: A Review," Thermal Conductivity 24 / Thermal Expansion 12, pp. 368–387 (Jan. 11, 1999).*

MTS–"Grips and Fixtures Catalog," ASTM E8, pp. 1–31 (in brochure), MTS System Corporation, 1986.*

ASTM D 648–56, Standard Method of Test for Deflection Temperature of Plastics Under Load, pp. 521–524 (1961).*

Seiko TMA Users Manual, Appendix–A, pp. A–1 through A–4 (prior to Jul. 9, 1998).*

* cited by examiner

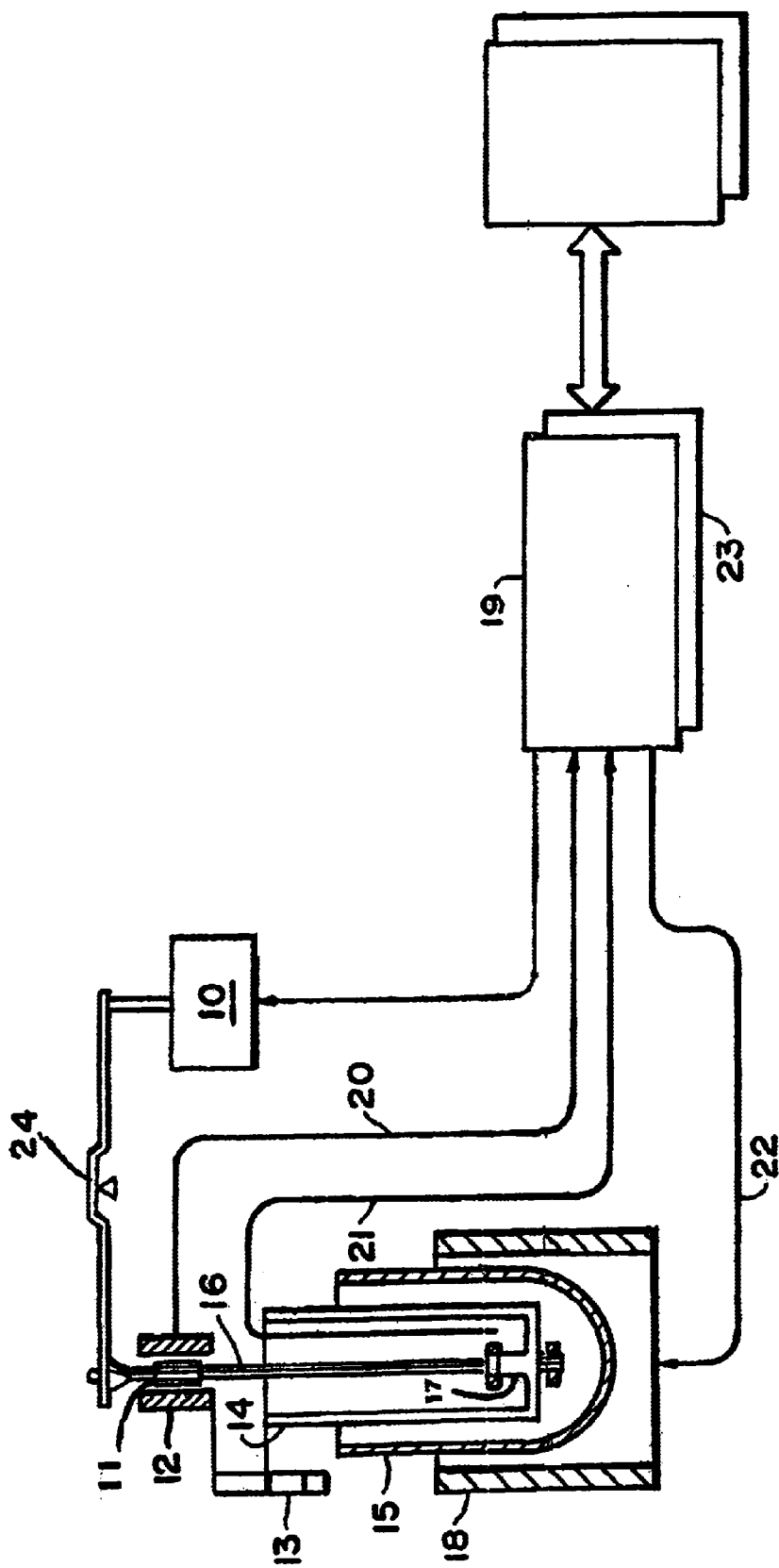
FIG. IB
PRIOR ART ial Appli-
METHOD FOR ACCOUNTING FOR CLAMP EXPANSION IN A COEFFICIENT OF THERMAL EXPANSION MEASUREMENT This application claims priority from Provisional Applications bearing Ser. Nos. 60/058,648 filed Jul. 11, 1997 and 60/059,891 filed Sep. 24, 1997.

BACKGROUND OF THE INVENTION

1. Technical Field of the Invention

The present invention is directed to increasing the accuracy of the measurement of thermal expansion coefficients (CTE) performed on thin film samples. More specifically, in accordance with the present invention, the CTE increased measurement accuracy is obtained using any of the following procedures: (a) by measuring the baseline using the same set-up used in the measurement; (b) by identifying a correction factor; (c) by using specific, low expansion clamps; or (d) by extracting the CTE from measurements of samples with various lengths.

2. Description of the Related Art

The testing of plastics is generally carried out for the same reasons as apply to the testing of other materials, namely to determine their suitability for a particular application, for quality control purposes or to obtain a better understanding of their behavior under various conditions. It is necessary for a manufacturer to be able to measure its performance with relation to other materials and thus be in a position to assess the market likely to be available to it.

The physical testing of plastics must be standardized if the comparison of physical data from two or more different sources is to have any meaning. The physical testing of plastics can be classified generally as (a) dimensional; (b) thermal; (c) mechanical; (d) electrical; and (e) optical. The results of physical tests carried out on a material often depend upon the ambient conditions of temperature, humidity, the size, shape and method of preparation of the test pieces and the techniques of measurement employed.

Testing of the thermal properties of plastics is important to give the plastic user some idea of the range of safe temperatures at which the plastic can be used. Some of the important thermal properties are thermal conductivity, coefficient of thermal or linear expansion, specific heat, softening point, heat distortion temperature and mold shrinkage.

The present invention relates to accurately measuring the CTE as this test is now advantageously used to test thin samples of polymers such as polyimide, and to a lesser extent, epoxy resins used in computer applications.

CTE's of materials are typically measured using a thermal mechanical analyzer (TMA). A TMA is an instrument used which is capable of measuring the displacement of a measuring probe with great accuracy in the compression mode, typical for CTE testing of rigid samples. The probe is in contact with a sample to be measured and detects changes in sample dimensions in probe direction and transmits results to a displacement detection unit. Test sample dimensions can change by the application of temperature or weight to the sample.

These dimensional changes may be time dependent. In the case of CTE measurements, the contact with the sample must be chosen so that the sample dimension does not change as a consequence of the probe; or if the sample dimension does change, such change is minimal and reproducible.

FIGS. 1A and 1B are generally equivalent with the exception that 1A operates in a compression mode, while 1B works in a tension mode such that the probe becomes the second sample holder. The sample in 1B is connected to the two holders by clamps shown in FIG. 3.

A typical TMA is depicted in FIG. 1A (prior art) comprising a probe (1), sample holder (2), heater (3), micrometer (4) (shown for illustrative purposes and not an essential part of a TMA), thermocouple (5), differential transformer (6), core (7), force generator (8). In a typical use, the plastic sample to be tested is held between sample holder (2) and probe (1). A force is applied to the sample, and the resulting changes in sample length are detected by the independently connected differential transformer (6) and core (7).

The TMA can be used in tensile mode for flexible samples pursuant to the present invention and is depicted in FIG. 1B (prior art). (Many identical elements are present in the structures depicted in FIG. 1A and FIG. 1B. To assist in an understanding of the structures of FIGS. 1A and 1B and to avoid confusion, the elements depicted in FIG. 1B which are also contained in FIG. 1A are indicated immediately after the numerical designation of the elements in FIG. 1B in brackets.) The unit comprises a load generator (10)(8), a core(11)(7), differential detector (12)(6), micrometer (13)(4), sample holder (14)(2), outer tube (15) not included in FIG. 1A, probe (16)(1), sample (17), and furnace (18)(3). The TMA module (19) receives a TMA/SS signal (20), a temperature signal from thermocouple (21) (5) and provides heater power (22). Also included in this apparatus is a means for processing software (23) used to provide certain instructions to the apparatus during operation as hereinafter described.

In this embodiment, with respect to the apparatus depicted in FIG. 1B, sample cylinder holder 14 is adjustably attached to differential transformer 12 via micrometer 13. When micrometer 13 is adjusted to an initial position, sample cylinder 14 is stationary with respect to detector 12. Probe 16 is connected to core 11 and sample 17. The top of probe (16) is also connected to a first end of balance arm (24). The other end of balance arm (24) is connected to electric load generator (10) which controls the load according to CPU guidance. The manner in which the force on the probe is generated is not relevant to the invention. There are a plurality of different ways that this may be accomplished. Differential detector (12) detects the movement of probe (16) as the sample (17) length changes, and outputs this as a TMA signal (20). Recorded signals are time, temperature, dimensional change and load.

There are a variety of probes that are used in the TMA depending upon what test is being conducted. The probes are configured for expansion, volume expansion, compression and penetration. In addition, accessories for tension and three point bending, and cubical are available. When combined with a dynamic loading program, a variety of applications not pertinent to this discussion are possible.

Presently, several ways of accomplishing contact of the probe to a sample exist. However, if the sample is a thin film, there is essentially only one way to guarantee continuous contact between the probe and the film while at the same time not bending the film.

In the method of the present invention, sample (30) is held by two clamps (31) and (32) as shown in FIGS. 2A and 2B (prior art front and side views respectively). FIGS. 2A and 2B show that top clamp (31) is held by or connected to probe (33) while bottom clamp (32) is stationary or fixed to stationary sample holder (34). Probe (33) and stationary sample holder support (34) are made from a material (such as quartz) which possesses a very small expansion coefficient so as not to interfere with the expansion of the sample.

Using the set up described above and depicted in FIGS. 2A and 2B, sufficient tensile force is applied to the probe so that the sample film (30) is under light tension. The length of the sample between the clamps (31) and (32) is recorded. For CTE measurements the sample is heated (cooled) and the probe displacement with temperature is measured.

FIG. 3 depicts a different side view of the elements depicted in FIG. 2B and includes a depiction of displacement sensor comprising calibrated measuring means (4) indicating one way in which measured displacement is determined. Elements (43) and (44) are made of a material with limited thermal expansion, such as quartz, and element (43) is subjected to a pulling force in direction (45). Distance L is the sample length. It is generally assumed that clamps (41) and (42), used to hold sample (40) do not contribute to the measured displacement. This is specifically stated in the user manual of one such instrument; (See: *Seiko TMA Users Manual*, Appendix-A, A-3).

FIG. 3 is identical to FIG. 2B with the exception that it adds a side view depiction of a graduated measurement scale 49 which indicates the extent of measured displacement.

A computer analysis software program collects displacement and temperature values. Often, time values are collected. Various software routines are used to extract and calculate the CTE for the particular sample tested. The CTE is computed as the difference of measured displacement D1, at temperature T1, and displacement D2, at temperature T2, divided by the difference between T1 and T2 and is exemplified by the expression: CTE =(D1–D2)/(T1–T2) [units of ° C.$^{-1}$]; wherein [D1–D2] is called the measured overall displacement (MD) (also referred to as (OD)); and T1–T2 is called the temperature range ($\Delta$T).

In order to obtain accurate values, the TMA must be well calibrated. This calibration includes collections of baselines and other instrument parameters which are conveniently incorporated into the software to obtain accurate data during measurements performed on samples.

In the electronics industry the matching of CTEs of dissimilar materials is of great importance because mismatch of the CTE of the various materials comprising an electronic device such as a memory or logic chip or an electronic package leads to stresses which influence the durability and performance of the device. Of particular importance is the measurement of materials with CTEs in the vicinity of the CTE of silicon (2.6 ppm/° C.).

In order to provide for the demands of the electronic industry, the chemical industry has responded by synthesizing polymeric materials which exhibit CTEs that match the 2.6 ppm/° C. value of silicon noted above. While silicon can be measured using compression mode CTE measurements, the CTE of these newly developed polymer films can only be measured directly in the tension mode. The reason for this is that in many polymer films, the CTE is a function of film thickness. Thus, thicker films which could be measured by other means will not give the required CTE values.

The thickness of the samples used in accordance with the present invention is in the range of between about 1 mm to 1 $\mu$m, preferably between about 150 $\mu$m and 5 $\mu$m.

Laboratory measurements have established that CTEs measured with the above-described tension mode do not give accurate results. Errors for materials such as silicon, were off by as much as 480%, even with a well calibrated instrument. Errors varied with sample length.

It is an object of the present invention to provide a method which allows accurate measurements of the CTE of thin films using the tensile mode. In particular, the present invention describes methods using the tensile mode that allow accurate measurement of the CTE of films with low expansion coefficients, that is between about –25 and +50 ppm/° C.

SUMMARY OF THE INVENTION

The predicate for the present invention is the discovery that in the course of determining the CTE of materials using a TMA, the clamps used in the TMA apparatus to hold the sample, contribute to the overall observed dimensional change of the sample. This dimensional change phenomenon is attributable to the fact that the clamps expand with heating and contract with cooling. The absolute values of the clamp displacement contribution to the overall value of the CTE of a sample is small. The accuracy of the CTE for samples with large CTE's is therefore not greatly influenced by the clamp displacement contribution.

However, clamp displacement can be a considerable portion of the dimensional change observed for samples with small CTE's. The present invention, as disclosed herein, eliminates, minimizes, or adjusts for the clamp expansion in order to obtain accurate CTE's.

The present invention discloses a plurality of ways to eliminate the influence of clamp dimensional changes on the displacement measurement during the measurement of the CTE of samples in tension using the TMA apparatus.

In one embodiment, clamp dimensional changes are eliminated by making clamps from a material with a CTE close to zero.

In a second embodiment, clamp dimensional changes, i.e. expansion or contraction, during the process are accounted for by fabricating the clamps from a material with a known, fixed CTE, thereby eliminating the influence of the CTE of the clamp material. Additionally, the clamps can be fabricated from a material that possesses a CTE that is identical for heating and cooling.

In another embodiment, the clamps are fabricated from a material having a CTE that changes linearly in the range of operation. In this embodiment, actual clamp dimensional changes during the measurement procedure must be taken into account. This is achieved by subtracting a predetermined and prerecorded baseline (value) from the test measurement results. In another embodiment CTE measurement for various sample lengths are conducted and the slope of a straight line through points on a MD (measured displacement)/$\Delta$T (temperature range of displacement measurement) vs. sample length plot is obtained. The slope yields the corrected CTE.

Finally, clamp dimensional changes can also be taken into account indirectly by obtaining a clamp contribution factor (CDC) which allows one to correct measured displacements to result in the correct CTE.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there is illustrated and described, the preferred embodiments of the invention.

BRIEF DESCRIPTION OF THE DRAWINGS

Further objects, features, and advantages of the present invention will become apparent from a consideration of the following detailed description of the invention when read in conjunction with the figures comprising the drawings, in which:

FIG. 1B is a depiction of an existing TMA apparatus using the tensile mode.

DETAILED DESCRIPTION OF THE PREFERRED EMBODIMENT

Figure 1A:
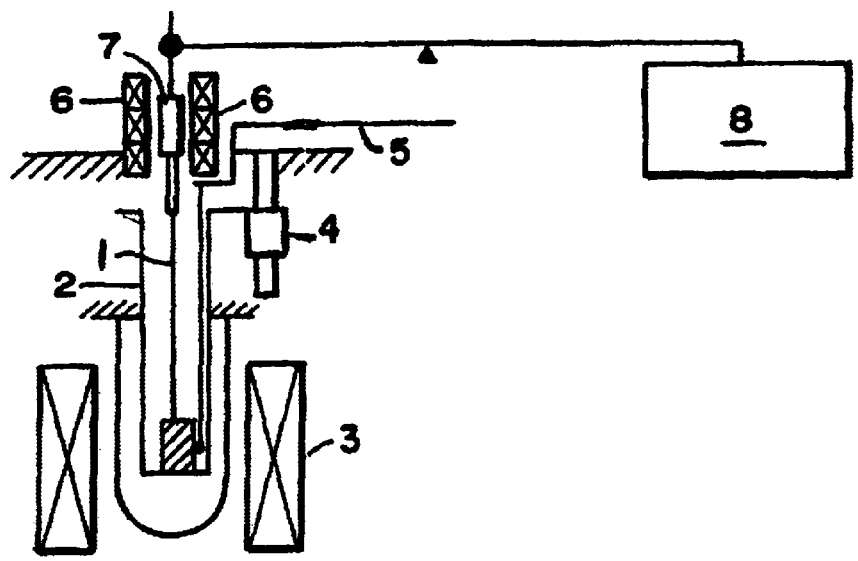
FIG. 1A is a depiction of a prior art TMA using expansion mode.
Figure 3:
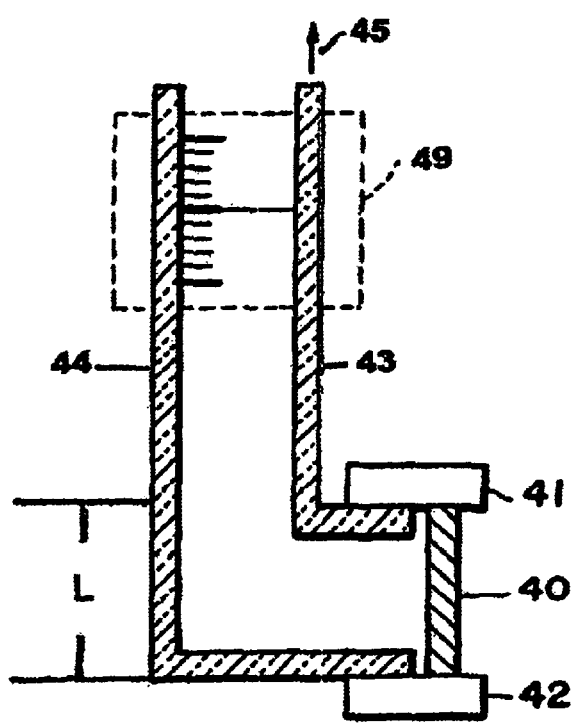
FIG. 3 is a schematic of the TMA of FIG. 2B including measurement means.
Figure 2A:
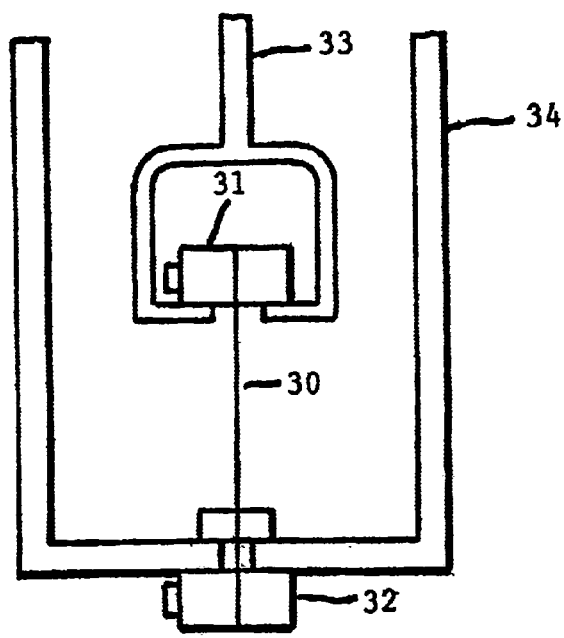
FIG. 2A is a sideview schematic of the tension mounted sample for the measurement of the CTE of a thin sample in a TMA.
Figure 2B:
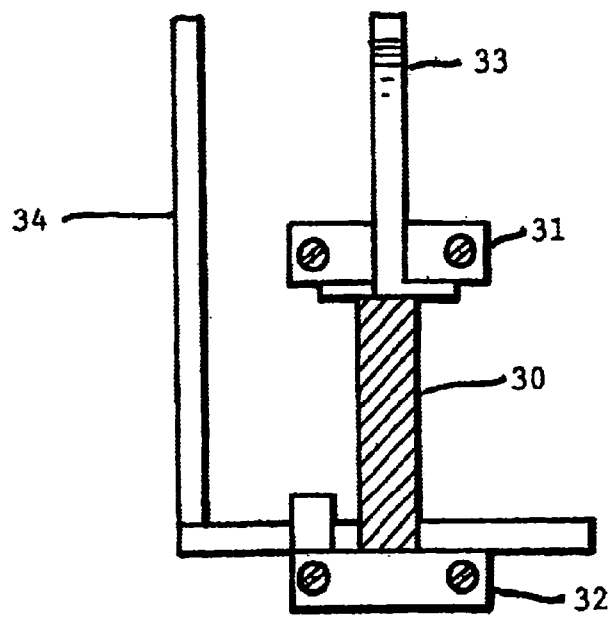
FIG. 2B is a front view schematic of the tension mounted sample for the measurement of the CTE of a thin sample in a TMA.

A first embodiment of the invention eliminates or minimizes the expansion of the clamps used in a TMA apparatus such as is depicted in FIG. 1B and FIGS. 2A and 2B. The material from which the clamps are fabricated has a coefficient of thermal expansion between about 0 and 20 ppm/°C. The object of the present invention is achieved by making the clamps out of a very low CTE material such as quartz or Invar which is an alloy having about 63.8% Fe, 36% Ni and 0.2 C. Other materials which may conveniently be used are ceramics, and molybdenum. When such low CTE material (s) is used, the measured CTE is virtually the actual CTE of the measured material. In general, under ideal conditions, a clamp material is chosen which possesses a CTE value that is close to zero during heating and cooling.

Within the purview of the first embodiment, and as a related feature of that aspect of the invention, the clamps in the TMA apparatus are made from materials with known CTE values. In this feature, a clamp material is chosen which possesses a linear CTE over the temperature range of the measurements taken.

Figure 5:
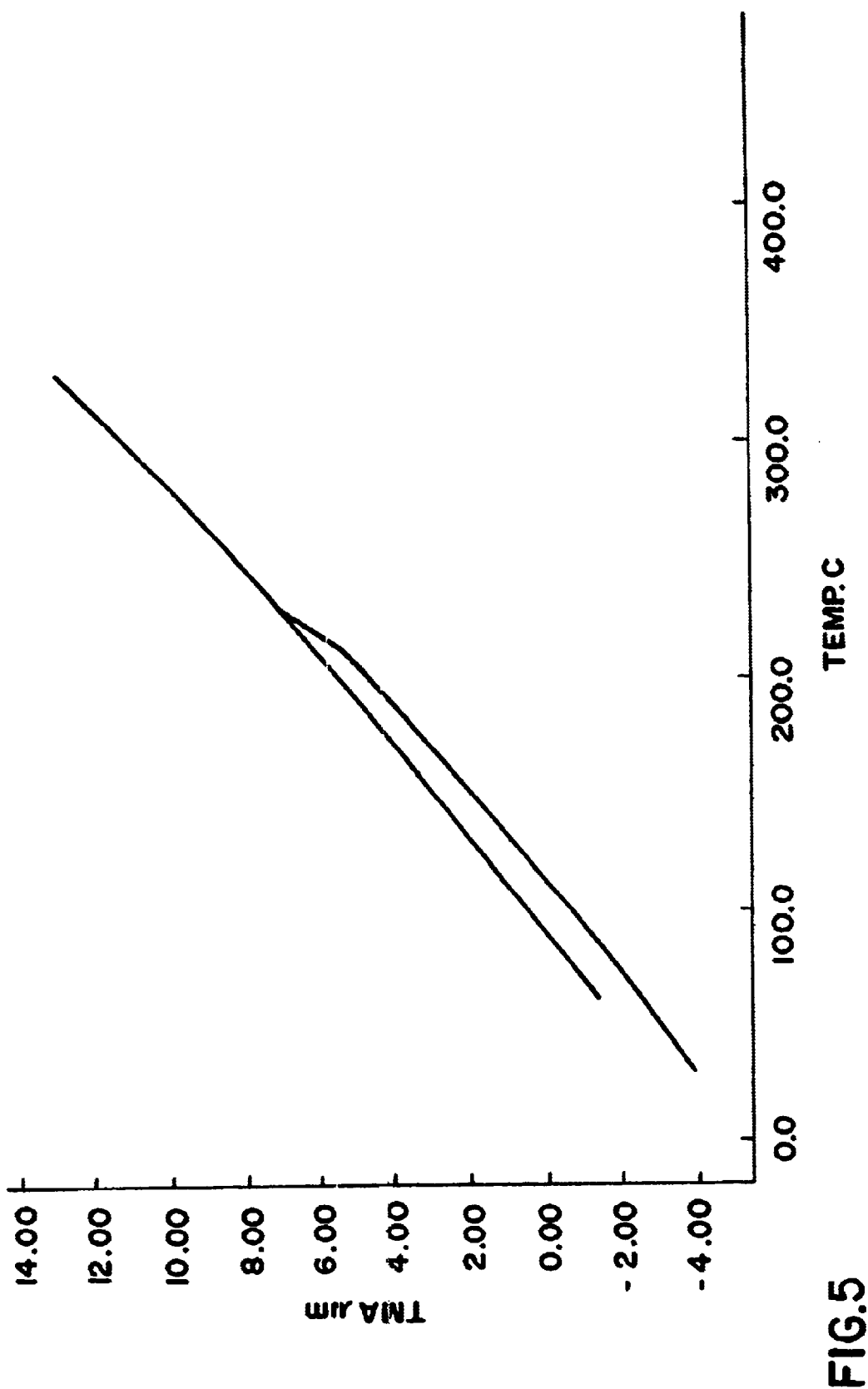
FIG. 5 is a graph showing the CTE measurement of the clamps in compression showing clamp expansion during heating and cooling, and shows a hysteresis between heating and cooling.

FIG. 5 shows the CTE behavior of a currently used clamp which exhibits a transition thus having dimensions that are not identical during heating and cooling. It is preferable to use a clamp material which possesses a small CTE and the identical CTE during heating and cooling.

Figure 4:
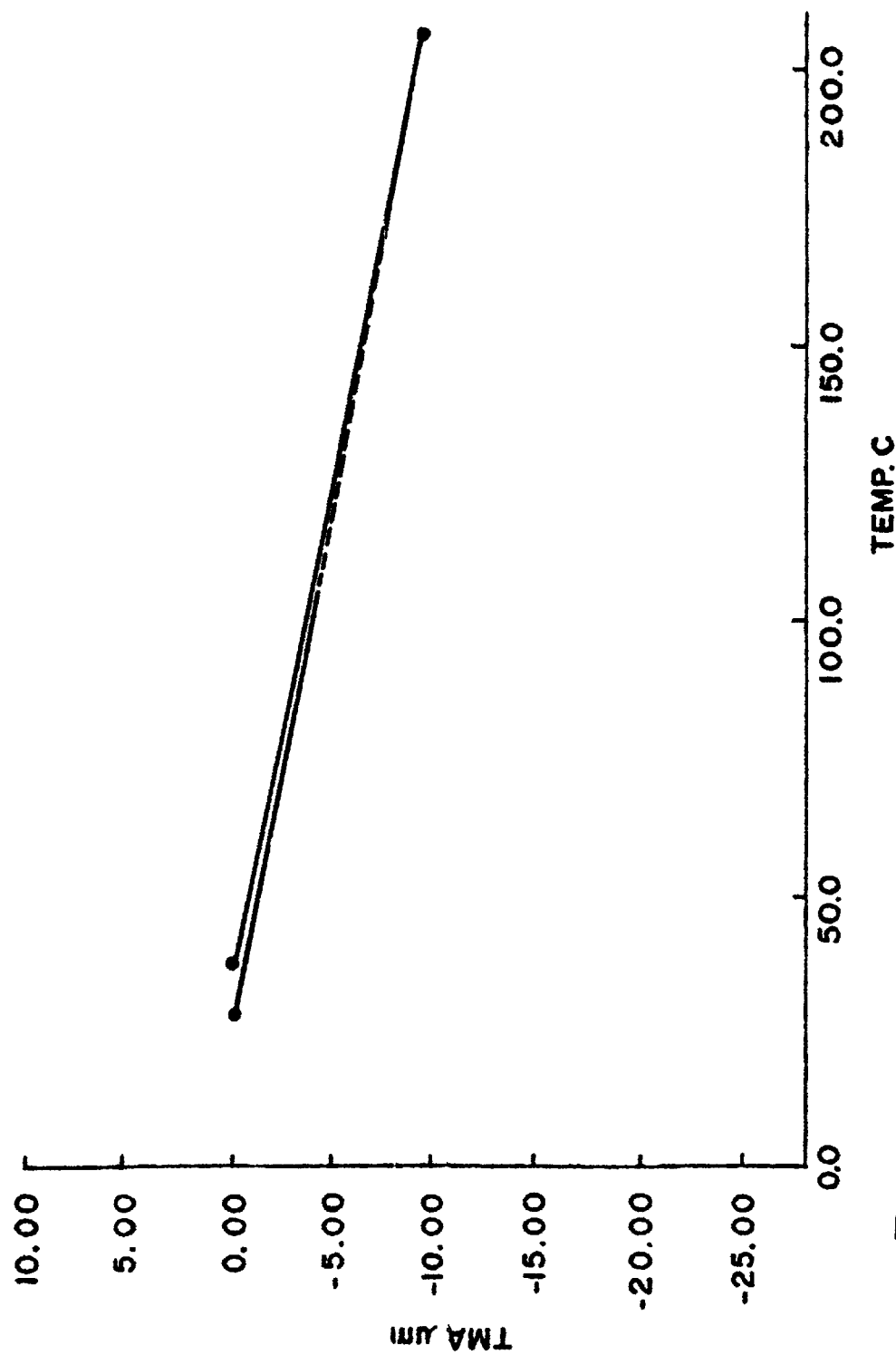
FIG. 4 is a graph depicting a baseline measured with a quartz sample using commercial clamps.

Referring to the drawings, the clearly visible metal phase transition is responsible for the difference in the heating baseline and the cooling baseline found in FIG. 4. Clamps made from such materials with the specified phase transition are not desirable. FIG. 5 depicts the difference between heating and cooling which is due to a metal phase transition in the clamps.

In a second embodiment of the invention, the influence of the clamp expansion is taken into account during the analysis of the raw data. Optionally, this can be done externally or internally.

In the external case, the user measures a baseline and prepares a functional relationship as shown in FIG. 4, which is used to correct each subsequent measurement. Preferably, the user-measured baseline becomes part of an internal baseline correction routine.

In the "internal" case, the data is analyzed by the TMA manufacturer and included in the software provided with the machine prior to the sale to the user. For example, the baseline is measured by the manufacturer using a silicon or quartz sample. The resulting information is stored in the software and is automatically subtracted when the CTEs are calculated.

In another embodiment of the invention, the user or equipment manufacturer determines a clamp displacement contribution (CDC) factor. Once determined, this factor is used to correct all measured displacement values or to correct the overall displacement measured in a given temperature range. The CDC factor can be used subsequently to modify the CTE measurement by the user; or it can become part of an internal correction applied to all CTE measurements obtained by tensile mode. In the latter case the user does not need to be aware of the procedure.

EXAMPLE 1

Figure 6:
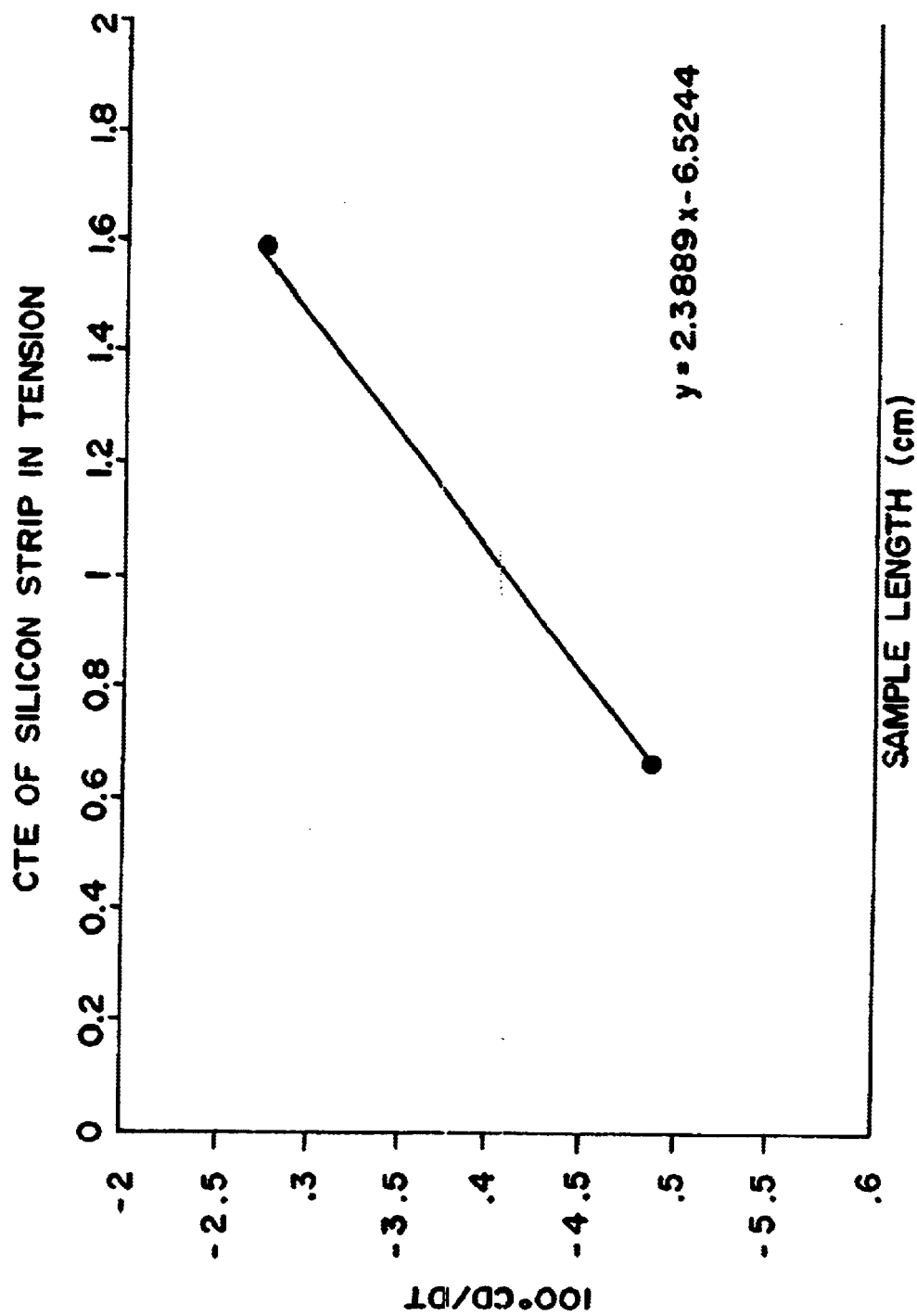
FIG. 6 is a plot of overall displacement MD (in $100\mu$), divided by the temperature range over which the measurement was taken, ($\Delta T$ in °C.), versus the sample length in cm.

The method of present invention for increasing the accuracy in determining the coefficient of thermal expansion of a silicon sample material using a thermal mechanical analyzer apparatus (TMA) was employed on a sample having dimensions of 20 mm length, 3 mm width and 1 mm thickness. The TMA was of the types depicted in FIGS. 1A or 1B and possessed a probe, sample holder, heater, micrometer, thermocouple, differential transformer, core, force generator, analysis software and had top clamp and bottom clamp elements. The clamps were made from stainless steel; the CTE behavior is shown in FIG. 6. The silicon sample to be measured was held between the top and bottom clamps, applying a tensile force to said top clamp so that said sample film is under light tension, i.e. about 10 g., and the displacement was measured.

With respect to the tensile force applied to the sample, the load needs to be chosen such that the sample will not deform within the given temperature range. In general, the load applied is between about 2 g. and about 100 g., preferably between about 10 g. and 20 g. This range is preferred because it has been found to be the range at which the force is sufficiently large not to cause displacement by vibrations and is not large enough to cause permanent sample deformation. A specific example is that a sample having a thickness of $10\mu$ is placed under a load of 10 g.

Thereafter the silicon sample was heated and cooled and the displacement of said sample was measured. In a separate operation, the silicon sample length was changed and the measurement steps were repeated. Taking the data generated from both experiments, the overall displacement over the temperature range was recorded and plotted against the sample length.

More particularly, as noted, the CTE measurement is performed for at least two sample lengths (L1, L2, etc . . . ) of a material over an identical temperature range ($\Delta T$). The measured overall displacement (MD1, MD2, etc . . . ) divided by the temperature range ($\Delta T$), for which the displacement was measured, is plotted against the sample length (L1, L2, etc . . . ). The slope of the straight line through the points of this plot is the correct CTE of the sample. The slope from this operation is depicted in FIG. 6. FIG. 6 is a plot of 100*(MD)/($\Delta T$) versus the silicon strip length in cms.

The slope can also be obtained by linear regression analysis. The slope as determined from the plot in FIG. 6 obtained pursuant to this Example 1 records the CTE of silicon as 2.4 ppm/° C. This measured result is substantially identical to the literature value of silicon which is 2.6 ppm/° C.

EXAMPLE 2

Figure 7:
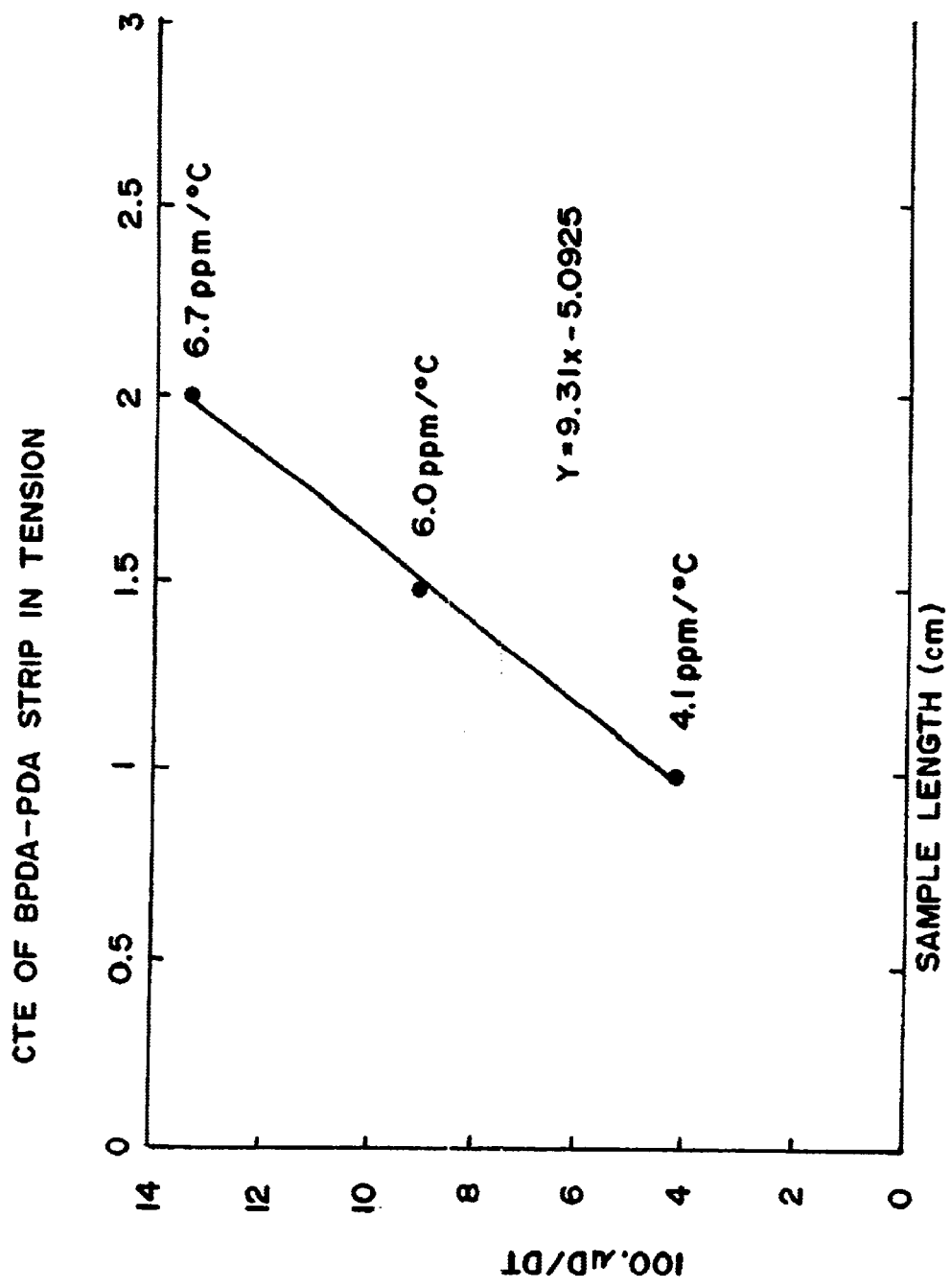
FIG. 7 shows a plot of measured displacement, MD (in 100 micrometers), divided by the temperature range over which the measurement was taken, ($\Delta T$ in °C.), versus the BPDA-PDA sample length in centimeters for a sample with unknown CTE.

In another example of an embodiment of the present invention, using the apparatus and procedure described above in Example 1, a sample BPDA-PDA strip with an unknown CTE was measured using sample length variations. Again, MD/$\Delta$T values are measured for a variety of sample lengths and plotted against the latter. FIG. 7 shows a plot of measured displacement, MD (in 100 micrometers), divided by the temperature range over which the measurement was taken, ($\Delta$T), versus the BPDA-PDA sample length in centimeters for a sample with unknown CTE.

FIG. 7 also shows the CTE values that were obtained for each sample length using the prior art instruments/procedure without any corrections. These are indicated for each sample length. The correct CTE for this BPDA-PDA strip is 9.31. This demonstrates that the errors in CTE values can exceed 100% in the example at hand.

EXAMPLE 3

Figure 8:
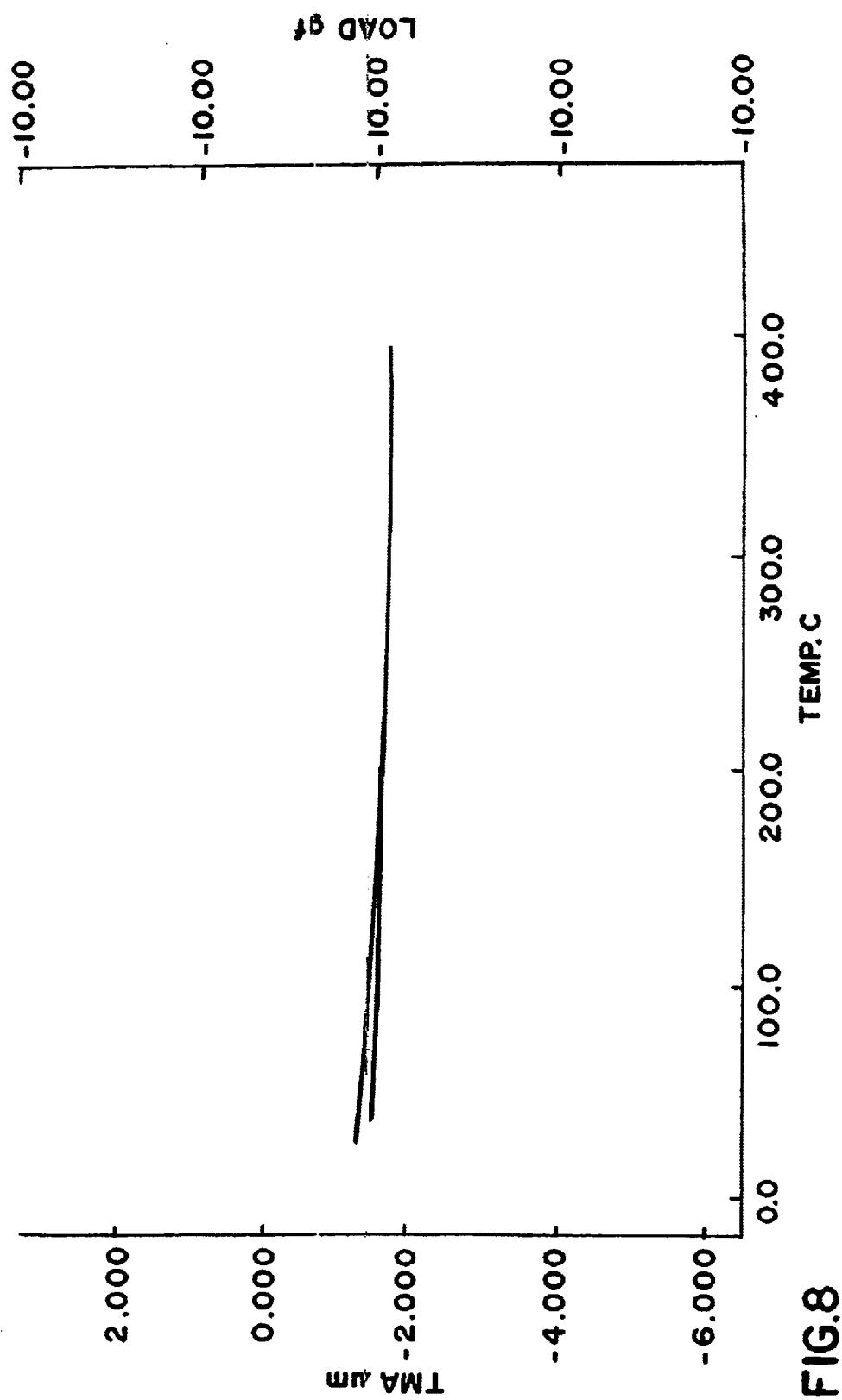
FIG. 8 shows the displacement vs temperature curve for a strip of quartz in tension after baseline correction.

Another method was used wherein a baseline was measured using a quartz standard and the current stainless steel clamps. Using the apparatus and procedure described above in Example 1, a quartz sample, 0.8 mm thick, 3 mm wide and 20 mm long, was mounted in the clamps and loaded into the TMA and a load of 10 g. was applied. The sample was heated at a low heating rate (2° C./min) to insure that the sample was in thermal equilibrium with the surroundings and was cooled at the same low rate. It is noted that heating rate is not significant when samples are only 10 $\mu$m thick as long as the rate is below 2° C./min. The measurement of this standard was continued until subsequent runs were identical. The displacement versus temperature curve of the last run was stored to be used as a baseline. FIG. 8 shows the displacement vs temperature curve for a strip of quartz in tension after baseline correction. There is a 0.2$\mu$ difference start and end; and between low and high temperature. This displacement difference can be neglected and will guarantee a very accurate CTE for samples using this baseline.

This baseline is also conveniently described by a polynomial, and can be incorporated into the software. A sample with unknown CTE and of the same length as the previously measured standard is now measured over the same range of temperature. The previously recorded polynomial baseline is subtracted from the displacement versus temperature plot of the unknown sample. Prior art methods to extract the CTE from this corrected plot are used to obtain the correct CTE value as shown in FIG. 8.

EXAMPLE 4

From the length variation measurements described in Example 3 above, a factor designated as the clamp displacement contribution (CDC) can be extracted. As shown hereinafter, the CDC factor can be used to obtain the correct CTE of unknown samples.

The straight line in the MD/$\Delta$T versus L (observed displacement vs. sample length) plot of FIG. 6 is described by:

$$MD/\Delta T = CTE*L + CDC$$

From this equation it is apparent that several methods exist to obtain the CDC factor. The CDC factor can be used to correct the displacement data and to obtain the correct CTE for any given sample.

One way to obtain the CDC factor is by determining the intersection of the line in the MD/$\Delta$T versus L plot, with the MD/$\Delta$T axis, i.e., the point at which L=0. The value of MD/$\Delta$T is then the value of the CDC.

Another way to obtain the CDC value is by measuring a standard with a linear CTE having a known value, wherein the measurement is taken in the tensile mode. After the length L is recorded, measurements are run until reproducible results are achieved. The measured sample displacement (MD) in the temperature range of interest is divided by said temperature range ($\Delta$T). From the resulting value, the product of the CTE of the standard and L is subtracted to obtain the Clamp Displacement Contribution (CDC) factor according to the equation:

$$(MD/\Delta T) - CTE*L = CDC$$

Corrected CTE's for samples with unknown CTE can be obtained with the knowledge of the CDC factor using the following calculation.

The MD of the unknown sample is divided by the DT in which the MD was measured. The CDC factor is subtracted and the resultant value is divided by sample length, L, according to:

$$(MD/\Delta T - CDC)/L = \text{corrected CTE of unknown sample}$$

Clamp correction factors can also be calculated from runs with a sample having known CTE (in ppm/° C.). The equation used is then:

$$CDC = (CTE\,(known) - CTE\,(measured))*L/1000$$

CDC factors were calculated from the experiments using a fused quartz standard. The CDC values for various temperature ranges are given in Table 1 hereinafter. It can be seen that the variation of CDC factors is between 4–5%. This indicates that this method will give CTE values with an acceptable accuracy of below 5% for samples with a CTE of above 2 ppm/° C. as long as the sample length is about 20 mm. For shorter samples, the error will increase.

This method can be incorporated into the software of the instrument to obtain corrected CTEs of unknown samples. The results of the experiments are set forth in Table 1.

TABLE 1

| CLAMP DISPLACEMENT CONTRIBUTION FACTORS | | | | |
|---|---|---|---|---|
| Temperature Range | Run 6 | Run 5 | Run 4 | Run 3 |
| Heating ° C. | | | | |
| 40–115 | — | 0.06315 | 0.07080 | 0.07124 |
| 30–115 | 0.05955 | — | — | — |
| 125–200 | 0.06083 | 0.05298 | 0.05189 | 0.06333 |
| 200–300 | 0.06407 | 0.06242 | 0.05850 | 0.06762 |
| 300–400 | 0.06476 | 0.06293 | 0.06054 | 0.06906 |
| 400–480 | | 0.05403 | 0.05297 | 0.06795 |
| Cooling | | | | |
| 40–100 | 0.06578 | 0.06966 | 0.07217 | 0.06573 |
| 100–200 | 0.06621 | 0.06749 | 0.06251 | 0.06954 |
| 200–300 | 0.07038 | 0.07227 | 0.06625 | 0.07310 |
| 300–400 | 0.07266 | 0.07652 | 0.07392 | 0.08112 |
| 400–480 | — | 0.07923 | 0.07778 | 0.09537 |

While the present invention has been described with respect to preferred embodiments, numerous modifications, changes, and improvements will occur to those skilled in the art without departing from the spirit and scope of the invention.

Thus, while there have been shown and described and pointed out fundamental novel features of the invention as applied to currently preferred embodiments thereof, it will be understood that various omissions and substitutions and changes in the form and details of the method and apparatus illustrated, and in their operation, may be made by those skilled in the art without departing from the spirit of the invention. In addition it is to be understood that the drawings are not necessarily drawn to scale but that they are merely conceptual in nature. It is the intention, therefore, to be limited only as indicated by the scope of the claims appended herewith.

What is claimed is:

1. A method of increasing the accuracy in determining the coefficient of thermal expansion of a thin film sample material using a thermal mechanical analyzer, said thermal mechanical analyzer having a probe, sample holder, heater, thermocouple, differential transformer, core, force generator, analysis software and having two clamps to hold said thin film sample comprising a top clamp element and a bottom clamp element; said thin film sample material having a top and a bottom, initially securing said top and said bottom of said thin film sample material between said top and bottom clamps respectively, then measuring the length of said thin film sample material from said top clamp to said bottom clamp, fastening said top clamp to said probe, and fastening said bottom clamp to said sample holder; applying a tensile force to said top clamp so that said thin film sample material is under light tension, whereupon said thin film sample material is heated and cooled and a resulting relative displacement of said thin film sample material is measured, and the coefficient of thermal expansion test measurement result is determined according to the formula computing the difference of measured displacement D1, at temperature T1, and displacement D2, at temperature T2, divided by the difference between T1 and T2 according to CTE=(D1−D2)/(T1−T2), said clamps being fabricated from a material different from said thin film sample material that eliminates the influence of the thermal expansion or contraction of said clamp on said measurement of the coefficient of thermal expansion.

2. The method defined in claim 1 wherein said material from which said clamp is fabricated, has a coefficient of thermal expansion of substantially zero.

3. The method defined in claim 1 wherein said material from which said clamp is fabricated, has a coefficient of thermal expansion between about 0 and 20 ppm/° C.

4. The method defined in claim 1 wherein said thermal mechanical analyzer includes a micrometer.

5. The method defined in claim 1 wherein said material from which said clamp is fabricated is fused silica.

6. The method defined in claim 1 wherein said material from which said clamp is fabricated is Invar alloy having about 63.8% Fe, 36% Ni and 0.2 C.

7. The method defined in claim 1 wherein said material from which said clamp is fabricated is molybdenum.

8. The method defined in claim 1 in which the actual value of the CTE of the clamps is known and the clamp dimensional changes are taken into account by subtracting said actual value from said test measurement results to obtain an accurate measurement of coefficient of linear expansion of said sample.

9. The method defined in claim 1 in which the material from which the clamp is fabricated possesses a linear coefficient of thermal expansion over the temperature range at which the coefficient of thermal expansion test measurement result is determined.

10. The method defined in claim 1 wherein said material from which said clamp is fabricated, has a coefficient of thermal expansion that is identical during said heating and cooling of said film.

11. The method defined in claim 8 wherein said material from which the clamp is fabricated also possesses a linear coefficient of thermal expansion over the temperature range at which the coefficient of thermal expansion test measurement result is determined.

12. The method defined in claim 8 wherein said material from which said clamp is fabricated, in addition has a coefficient of thermal expansion that is identical during said heating and cooling of said film.

13. The method defined in claim 9 wherein said material from which said clamp is fabricated, in addition has a coefficient of thermal expansion that is identical during said heating and cooling of said film.

14. The method defined in claim 11 wherein said clamp is formed from a material selected from the group consisting of ceramic, stainless steel, Invar alloy having about 63.8% Fe, 36% Ni and 0.2 C, molybdenum, platinum, silver and aluminum.

15. The method defined in claim 12 wherein said clamp is formed from a material selected from the group consisting of ceramic, stainless steel, Invar alloy having about 63.8% Fe, 36% Ni and 0.2 C, molybdenum, platinum, silver and aluminum.

16. The method defined in claim 13 wherein said clamp is formed from a material selected from the group consisting of ceramic, stainless steel, Invar alloy having about 63.8% Fe, 36% Ni and 0.2 C, molybdenum, platinum, silver and aluminum.

17. The method defined in claim 1 wherein prior to said measurement of relative displacement between said temperatures T1 and T2 of said thin film sample, a standard thin film sample material is measured using said exact method and elements to be used for the temperature range of interest, wherein said standard thin film sample material is formed of the same material as said probe and said clamps and said standard measurement technique is used as baseline for subsequent coefficient of linear expansion measurement of said sample.

18. The method defined in claim 17 wherein said standard is fused silica or quartz.

19. The method defined in claim 17 wherein said standard baseline measurement is converted into data which is stored in electronic form and is used in conjunction with said thermal mechanical analyzer.

20. The method defined in claim 17 wherein said baseline is defined by a polynomial.

21. The method defined in claim 17 wherein said baseline is subtracted from said coefficient of thermal expansion test measurement result performed subsequent to said baseline determination.

22. The method defined in claim 20 wherein said polynomial is used to determine a baseline correction on said measurement.

23. The method defined in claim 17 wherein said baseline measurements are contained within said thermal mechanical analyzer at a subsequent time said method is run.

24. The method defined in claim 23 wherein said standard is fabricated from the same material as said probe and clamps.

25. The method defined in claim 24 wherein said standard is fabricated from a material selected from the group consisting of fused silica and quartz.

26. The method defined in claim 23 wherein said baseline measurement is stored in electronic form in said analysis software of said thermal mechanical analyzer.

27. The method defined in claim 26 wherein said stored baseline is subtracted from said measured displacement.

28. The method defined in claim 26 wherein said stored baseline is described by a polynomial.

29. The method defined in claim 8 wherein said coefficient of linear expansion measurements are performed on two said samples of unknown coefficient of linear expansion having lengths L1 and L2, said measured displacements MD1, MD2 are determined and divided by the temperature range $\Delta T$ over which displacements were measured, and values determined using MD1/$\Delta T$ and MD2/$\Delta T$ are plotted as a function of L1, L2, the slope of the resulting straight line through said resulting points being the coefficient of thermal expansion of said sample.

30. The method defined in claim 29 wherein a linear regression is conducted to obtain the coefficient of thermal expansion.

31. The method defined in claim 29 wherein the Clamp Displacement Contribution (CDC) factor is determined by noting the intercept of the line with the D/$\Delta T$ axis at L=0.

32. The method defined in claim 29 wherein the Clamp Displacement Contribution (CDC) factor is determined by noting the sample length (L) of said standard and the measured displacement (MD) for said standard is divided by the temperature range ($\Delta T$) over which the displacement is measured and the product of (L)×(CTE) of the standard is subtracted from (MD)/($\Delta T$).

33. The method defined in claim 32 wherein said CDC factor is subtracted from OD (unknown sample)/$\Delta T$ with the resultant parameter divided by the length of the unknown sample to obtain the coefficient of thermal expansion of said sample.

34. The method defined in claim 32 wherein the product of said CDC factor with $\Delta T$ is subtracted from OD (unknown sample) and the resultant value is divided by the length of the unknown sample and $\Delta T$ to obtain the correct coefficient of thermal expansion of said sample.

35. The method defined in claim 29 wherein said CDC factor is subtracted from OD (unknown sample)/$\Delta T$ with the resultant value divided by the length of the unknown sample to obtain the correct coefficient of thermal expansion of said sample.

36. The method defined in claim 32 wherein said CDC factor has been integrated into the thermal mechanical analyzer prior to determination of the coefficient of thermal expansion.

37. The method defined in claim 32 wherein said CDC factor is incorporated into said method to correct the measured displacement during the method of determining an accurate coefficient of thermal expansion.

38. The method defined in claim 32 wherein said CDC factor is integrated into said analysis software to correct the measured displacement during the method of determining an accurate coefficient of thermal expansion.

39. The method defined in claim 32 wherein said CDC factor is integrated into said measurement software to correct the measured displacement during the method of determining an accurate coefficient of thermal expansion.

* * * * *